(12) United States Patent
Nadenik et al.

(10) Patent No.: US 6,518,420 B2
(45) Date of Patent: Feb. 11, 2003

(54) PRECIPITATION PROCESS OF 7-AMINOCEPHALOSPORANIC ACID (7-ACA)

(75) Inventors: Petr Nadenik, Wörgl (AT); Helmut Wagner, Kramsach (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 10/035,638

(22) Filed: Nov. 7, 2001

(65) Prior Publication Data

US 2002/0086992 A1 Jul. 4, 2002

Related U.S. Application Data

(63) Continuation of application No. 09/445,042, filed as application No. PCT/EP98/03278 on Jun. 2, 1998, now abandoned.

(30) Foreign Application Priority Data

Jun. 4, 1997 (AT) .................................. 951/97
Jun. 30, 1997 (AT) .................................. 1112/97

(51) Int. Cl.$^7$ .......................................... C07D 501/26
(52) U.S. Cl. ........................................ 540/219
(58) Field of Search .............................. 540/219

(56) References Cited

U.S. PATENT DOCUMENTS

| | | | | |
|---|---|---|---|---|
| 3,367,933 A | * | 2/1968 | Eardley | 540/219 |
| 3,507,860 A | * | 4/1970 | Wetherill | 540/215 |
| 3,507,862 A | * | 4/1970 | Stamper | 540/219 |
| 3,575,970 A | * | 4/1971 | Weissenberger | 540/219 |
| 3,594,370 A | * | 7/1971 | Higgins | 540/219 |
| 3,594,371 A | * | 7/1971 | McIntyre | 540/219 |
| 3,813,389 A | * | 5/1974 | Hayes | 540/219 |
| 3,840,532 A | * | 10/1974 | Hayes | 540/219 |
| 3,957,771 A | * | 5/1976 | Bormann et al. | 540/230 |
| 4,028,355 A | * | 6/1977 | Blackburn | 540/219 |
| 4,322,526 A | * | 3/1982 | Ascher | 540/230 |
| 5,679,789 A | * | 10/1997 | Clark | 540/349 |
| 6,165,976 A | * | 12/2000 | Backstrom | 540/303 |

FOREIGN PATENT DOCUMENTS

| | | |
|---|---|---|
| DE | 15 45 898 A | 4/1970 |
| DE | 22 22 094 A | 11/1973 |
| DE | 25 02 197 A | 7/1975 |
| DE | 30 02 659 A | 7/1980 |
| GB | 1 277 228 A | 6/1972 |
| GB | 1 421 199 A | 1/1976 |

OTHER PUBLICATIONS

European Phamacopoeia, Third Edition, p. 18, 1997.*
Academnic Press Dictionary of Science and Technology, Morris, ed., (Academic Press, 1991) pp. 1688, 1690.*
Hawley's Condensed Chemical Dictionary, 12th Edition (Van Nostrand Reinhold, 1993), p. 53.*
Webster's Third New International Dictionary (Merriam Webster, Inc, 1986) p. 815.*
Cieslak, Chemical Abstracts, vol. 90, No. 15, Abstract No. 121587p, p. 646, 1988.
Derwent Abstract AN 93–098389 (RO 102 148 A) (1991).
Derwent Abstract AN 94–200170 (WO 94 12504 A and WO 94 12501 A) (1994).
Oberhauser, T. et al., Tetrahedron, vol. 52, No. 22, "On the Stereochemical Purity of (+)–7–Aminocephalosporanic Acid," pp. 7691–7702 (1996).

* cited by examiner

Primary Examiner—Mark L. Berch
(74) Attorney, Agent, or Firm—Peter J. Waibel

(57) ABSTRACT

A process in the isolation of 7-aminocephalosporanic acid (7-ACA) from an alkaline, neutral or slightly acidic medium in the presence of an additive, e.g. selected from the group comprising organic carboxylic acid esters, polymeric glycols, polyacryls, amines and polyamines, melaminformaldehyde resins or amino acids and esters thereof to obtain 7-ACA agglomerates and or rosettes.

4 Claims, No Drawings

PRECIPITATION PROCESS OF 7-AMINOCEPHALOSPORANIC ACID (7-ACA)

This application is a continuation of application U.S. Ser. No. 09/445,042, filed Feb. 3, 2000, now abandoned, which is a 371 of PCT/EP98/03278 U.S. Ser. No. filed Jun. 2, 1998.

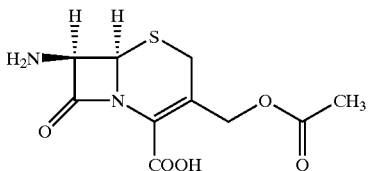

I

7-ACA is a key intermediate compound in the synthesis of many semi-synthetic cephalosporin antibiotics. It may e.g. be produced from cephalosporin C by cleavage of the amide function in position 7 of the ring sytem
- e.g. chemically, e.g. by conversion of the amide function into an imide chloride function which may be hydrolysed to give 7-ACA, e.g. in a strong acidic medium and precipitating 7-ACA, e.g. by adjustment of the pH (around the isoelectric point), e.g. by addition of a base; 7-ACA may be isolated in the form of rosettes and agglomerates;
- or enzymatically, e.g. by action of an acylase; or by conversion of cephalosporin C into glutaryl-7-aminocephalosporanic acid, e.g. by action of a D-amino acid oxidase, enzymatically hydrolysing a glutaryl-7-amino cephalosporanic acid to obtain 7-ACA, e.g. in a basic medium, neutral or slightly acidic medium, optionally purifying the reaction solution with an appropriate ion exchanger or adsorber resin, and precipitating 7-ACA, e.g. by adjustment of the pH (around the isoelectric point), e.g. by addition of an acid, e.g. HCl. In that case precipitated 7-ACA may be, however, in the form of very small, loose, needle-like crystals difficult to be isolated. Increasing purity of 7-ACA may result in still smaller crystals and addition of an organic solvent, e.g. a, e.g. lower, alcohol, e.g. methanol or a ketone, e.g. acetone, to the reaction mixture before the isolation of 7-ACA, which may improve the yield, again may result in considerably smaller crystals.

The present invention provides a process, e.g. which may by carried out on technical scale, wherein agglomerates or rosettes of 7-ACA may be formed on 7-ACA precipitation from an alkaline, neutral or slightly acidic medium which substantially improves isolation of 7-ACA, e.g. by filtration and centrifugation and additionally, 7-ACA obtained according to the present invention may be dried more quickly, e.g. which may result in a smaller amount of by-products compared with 7-ACA obtained according to a prior art process.

In one aspect the present invention provides a process for the production of rosettes or agglomerates of 7-ACA, e g. of formula I, characterized in, that 7-ACA is precipitated from an alkaline, neutral or slightly acidic medium in the presence of an additive, e.g. selected from a group comprising e.g. groups as defined below.

An additive according to the present invention may be a compound which on addition in a precipitation process of 7-ACA may cause formation of agglomerates and/or rosettes includes e.g. organic carboxylic acid esters,e.g. of formula

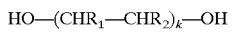  II, polymeric glycols, e.g. polyethylene and polypropylene glycols, e.g of formula

  III, polyacryls, e.g. of cationic, anionic or non-ionic polyacryls, including e.g. polacrylamides, e.g. of formula

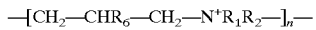  IV, amines and polyamines, e.g. of formulae

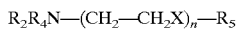  Va

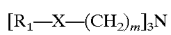  Vb $[R_1\text{—}X\text{—}(CH_2)_m]_3N$  Vc

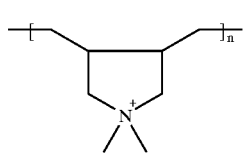

VIa or

VIb

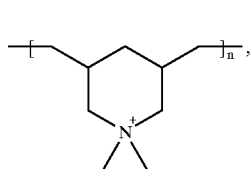

melamin-formaldehyde resins, e.g. of formula

VII

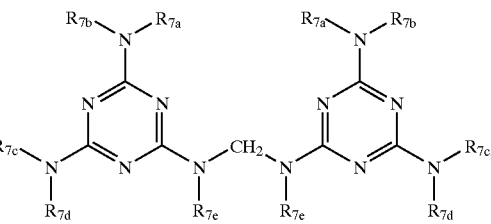

e.g. of a molecular weight of up to 1,000,000, e.g. 500,000 and amino acids and esters thereof, e.g. of formula

  VIII e.g. including mixtures of individual additives, e.g. as described above. An additive may be preferably an amino acid and esters therof, e.g. an amino acid such as e.g. lysine.

In formulae II, III, IV, Va, Vb, Vc, VIa, VIb, VII and VIII $R_1$, $R_2$, $R_4$ and $R_5$ independently of each other denote hydrogen, alkyl or aryl;

k denotes a whole number from 2 to 200;

X denotes —O— or —$NR_1$—;

$R_3$ has the meaning of $R_1$ or denotes a group of formula —$(CR_2R_4)_m$—Z

Z denotes amino, a sulphonyl group or a carboxylic acid group, e.g. of formulae

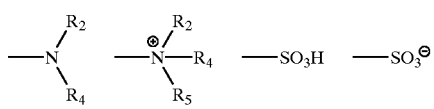

-continued

—COOH or —COO$^\ominus$;

m denotes a whole number from 0 to 6;
n denotes a whole number from 2 to 200,000;
$R_6$ represents hydrogen or hydroxy;
$R_{7a}$, $R_{7b}$, $R_{7c}$, $R_{7d}$ and $R_{7e}$ independently of each other denote hydrogen, —CH$_2$OH; or a group of formula

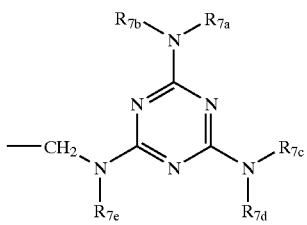

and $R_{10}$ denotes hydrogen, alkyl, aryl or a group of formula —(CH$_2$)$_m$—X—R$_5$.

If not otherwise defined herein, alkyl includes e.g. (C$_{1-22}$)alkyl, such as (C$_{1-8}$)alkyl, e.g. lower alkyl, such as (C$_{1-4}$)alkyl and aryl includes e.g. phenyl, naphthyl, such as phenyl.

Alkyl and aryl includes unsubstituted alkyl and aryl and alkyl and aryl substituted by groups which do not cause the formation of another compound than 7-ACA under precipitation conditions of 7-ACA in alkaline, neutral and slightly acidic medium; e.g. which do not chemically react with 7-ACA to form another compound. Preferably alkyl includes lower alkyl; aryl includes phenyl and substituted aryl includes substituted aryl, e.g. phenyl by hydroxy or alkyl e.g. lower alkyl. Amino includes unsubstituted amino or ammonium and substituted amino and ammonium, e.g. by alkyl.

In another aspect the present invention provides a process for the isolation of 7-ACA, e.g. of formula I from slightly acidic, neutral or alkaline solution, characterized in that 7-ACA is precipitated in the presence of an additive, e.g. selected from a group comprising groups as e.g. defined above, e.g. in an amount of 1 ppm to 10% in the slightly acidic, neutral or alkaline solution.

A process of the present invention may be carried out as follows:
7-ACA may be precipitated
  from slightly acidic, neutral or alkaline solution of 7-ACA, including e.g. a solution of 7-ACA in a solvent to which an acid is to be added for precipitating 7-ACA therefrom, e.g. a solution of 7-ACA having a pH which is above the isoelectric point of 7-ACA in a solvent; which is in contrast to a strong acidic solution of 7-ACA to which a base is to be added for precipitating 7-ACA therefrom, e.g. a solution of 7-ACA having a pH which is below the isoelectric point of 7-ACA in a solvent
  in the presence of an additive, e.g. selected from a group comprising groups as defined above, e.g. in the presence of seed crystals of 7-ACA, e.g. in the form of rosettes and/or agglomerates by addition of an acid.

An additive according to the present invention is known or may be produced analogously to known, e.g. conventional processes. A slightly acidic, neutral or alkaline solution of 7-ACA may be obtained e.g. by an enzymatic process as defined above. The concentration of 7-ACA in slightly acidic, neutral or alkaline solution is not critical and may vary within a broad range, including e.g. a rangeof, e.g. ca., 5 to 60 g/l, such as 10 to 50 g/l. An additive may be e.g. added to 7-ACA in slightly acidic, neutral or alkaline solution before addition of an acid or simultanously.

The amount of an additive according to the present invention is not critical, e.g. for ecological reasons a low amount of an additive, e.g. ca., 1 ppm to 10% (v/v) in respect with the amount of 7-ACA solution may be appropriate. In case of use of non-polymeric additives, such as e.g. organic esters as an additive an amount of, e.g. ca., 1% to 10% may be appropriate; in case of use of an amine, amino acid or ester thereof an amount of, e.g. ca., 0.01% to 10%, such as, e.g. ca., 0.05% to 5% may be appropriate, in case of use of a polymeric additives, e.g. such as polyacryls, polyamines, polymeric glycols e.g. ca. 1 to 100 ppm may be appropriate. Seed crystals of 7-ACA, e.g. as defined above, may be added to a solution or to a resulting crystal suspension of 7-ACA either prior to or simultaneously with an acid.

The process of the present invention may be carried out batchwise or continuously, in a broad temperature range, including e.g. −15° to 40° C., such as 0° to 25° C.

An appropriate acid includes inorganic acids, e.g. sulphuric acid, hydrochloric acid or phosphoric acid, or organic acids, e.g. acetic acid.

The acid is added in an amount which is sufficient that 7-ACA, e.g. in high yields, is precipitated from the solution. A pH of the reaction mixture of around the isoelectric point of 7-ACA in a solvent may be convenient, including, but not limited to, a pH of 2.5 to 6, such as 3.5 to 5.5. 7-ACA may precipitate on acid addition, e.g. in crystalline form. A crystall suspension obtained may be stirred, e.g. under adjustment of the pH around the isoelectric point in order to complete precipitation, e.g. under cooling.

7-ACA obtained, e.g. in crystalline form and in the form of agglomerates and/or rosettes may precipitate and may be isolated, e.g. as conventional, such as by filtration, centrifugation, washed as appropriate and dried. The drying temperatures may be low, e.g. 40° to 50°, e.g. under vacuum, and the drying times may be short, e.g. ca. 5 to 30, such as 10 to 20 hours.

The presence of an additive according to the present invention in the precipitaion of 7-ACA may surprisingly result in the formation of agglomerates or rosettes of 7-ACA, even in case that an organic solvent such as an alcohol or a ketone is present in the solution and even in case that highly pure 7-ACA, e.g. purified via an adsorber resin purification, e.g. with Amberlite XAD 1600$^R$, XE-714$^R$, Dianion HP21$^R$, Sepabeads SP825$^R$, SP850$^R$), or via an ion exchanger purification, e.g. with IRA 420$^R$. The filtration time of a 7-ACA crystal suspension in the presence of an additive obtained according to the present invention may considerably be reduced in comparison with the filtration time of 7-ACA obtained without the presence of an additive, e.g. from ca. 15 minutes to 1 minute and even below, such as of ca. 0.4 minutes.

The following examples are intended to illustrate the invention. Temperatures are given in degree Celsius and are uncorrected.

7-ACA is 7-aminocephalosporanic acid, e.g. of formula I.

EXAMPLES 1 to 14

General Procedure 142 ml of water and 2.2 g of 7-ACA in form of rosettes and/or agglomerates as a seeding material are placed in a precipitation reactor, and the pH is adjusted to 5.5 with 1 N NaOH. A solution of 25 g of 7-ACA in the form of a sodium salt, 708 ml of water with or without methanol (in ml) as set out in TABLE 1 below having a pH of ca. 7.0 is mixed with an additive as set out in TABLE 1 below and the mixture obtained is added dropwise to the mixture in the reactor under stirring over the course of ca. 25 minutes at ca. 18°. During addition of the 7-ACA mixture into the mixture in the precipitation reactor the pH of the reaction mixture obtained is adjusted to 5.5 by addition of 20% sulphuric acid. The pH of a suspension obtained is adjusted to 4.0, the suspension is cooled to 0° and stirred for ca. 1 hour. Crystalline 7-ACA obtained is filtrated off, washed with 120 ml of water, 120 ml of 70% methanol and 120 ml of methanol and dried in a vacuum (ca. 10 mbar) for ca. 16 hours at ca. 50°. The filtration times (in minutes) are summarised in TABLE 1 below.

TABLE 1

| Example | Methanol [ml] | Additive | Filtration time [min] |
|---|---|---|---|
| 1 | 212 | No additive | 15 |
| 2 | 212 | Polyacryl (amide) e.g. 6.5 ml 1% solution of P3-Ferrocryl 7262$^R$ | 2.1 |
| 3 | 0 | Polyacryl (amide) e.g. 6.5 ml 1% solution of P3-Ferrocryl 7262$^R$ | 1.6 |
| 4 | 0 | Organic carboxylic acid ester e.g. 49.5 ml Ethyl acetate | 2.1 |
| 5 | 0 | Organic carboxylic acid ester e.g. 10.6 ml Butyl acetate | 1.1 |
| 6 | 212 | Organic carboxylic acid ester e.g. 13.8 ml Butyl acetate | 2.4 |
| 7 | 212 | Organic carboxylic acid ester e.g. 64.4 ml Ethyl acetate | 2.9 |
| 8 | 177 | Polyacryl (amide) e.g. 0.8 ml 1% solution of Cysep 2411$^R$ (Cytec) | 0.8 |
| 9 | 177 | Polyamine e.g. 0.8 ml 1% solution of C 592$^R$ (Cytec) | 0.3 |
| 10 | 177 | Polyamine e.g. 0.8 ml 1% solution of C 567$^R$ (Cytec) | 0.4 |
| 11 | 177 | Polymeric glycol e.g. 3.2 ml 1% solution of PEG 300$^R$ (Fluka) | 2.1 |
| 12 | 177 | Amine e.g. 2.4 ml 1% solution of triethylene tetramine | 3.2 |
| 13 | 177 | Amine e.g. 0.8 ml 1% solution of tris-(2-amino-ethyl)amine | 3.2 |
| 14 | 177 | Amino acid e.g. 0.8 ml 1% solution of l-lysine | 3.3 |

EXAMPLES 15 to 18

General Procedure

A solution of 20.8 g of 7-ACA in the form of a sodium salt, 500 ml of water with or without methanol (in ml) as set out in TABLE 2 below having a pH of ca. 7.5 is placed in a precipitation reactor at room temperature and mixed with an additive as set out in TABLE 2 below. The pH of the mixture obtained is adjusted to 5.5 by addition of 20% sulphuric acid under stirring and kept for ca. 20 minutes. The pH of a suspension obtained is adjusted to 3.8, the suspension is cooled to 0° and stirred for ca. 1 hour. Crystalline 7-ACA obtained is filtrated off, washed with 100 of water, 100 ml of 70% methanol and 100 ml of methanol and dried in a vacuum (ca. 10 mbar) for ca. 16 hours at ca. 50°. The filtration times (in minutes) are summarised in TABLE 2 below.

TABLE 2

| Example | Methanol [ml] | Additive | Filtration time [min] |
|---|---|---|---|
| 15 | 150 | No additive | 14 |
| 16 | 100 | Organic carboxylic acid ester e.g. 9 ml 1 Butyl acetate | 1.5 |
| 17 | 150 | Polyacryl (amide) e.g. 6.5 ml 1% solution of Ferrocryl 7262$^R$ (Henkel) | 1.4 |
| 18 | 150 | Polyacryl (amide) e.g. 3.2 ml 1% solution of Rohafloc KF760$^R$ (Rhöm) | 3.0 |

What is claimed is:
1. A process for the precipitation of 7-ACA of formula

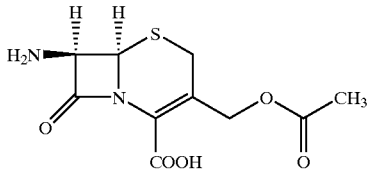

I comprising
   a) providing an alkaline, neutral or slightly acidic solution of the corresponding 7-ACA carboxylate with a pH above the isoelectric point of 7-ACA
   b) adding an acid to the solution in an amount sufficient to precipitate the 7-ACA in the presence of an additive being selected from the group consisting of organic carboxylic acid esters, polyacrylates, polymeric glycols and amino acids of formula

$R_{10}$—CH—(NR$_2$R$_4$)—COOR$_1$     VIII wherein $R_{10}$ denotes hydrogen, unsubstituted or substituted alkyl, unsubstituted or substituted aryl or a group of formula —(CH$_2$)$_m$—X—R$_5$, and R$_1$, R$_2$, R$_4$ and R$_5$ are the same or different and represent hydrogen, unsubstituted or substituted lower alkyl, phenyl, (mono-tri)hydroxyphenyl or lower alkylphenyl, X denotes —O— or —NR$_4$, and m is a whole number from 0 to 6.
2. A process according to claim 1 characterized in that the additive is lysine.
3. A process according to claim 1, characterized in that the additive is present in an amount of 1 ppm to 10% in the alkaline, neutral or slightly acidic solution with a pH above the isoelectric point of 7-ACA containing the corresponding 7-ACA carboxylate.
4. A process for the isolation of 7-aminocephalosporanic acid (7-ACA) from an alkaline, neutral or slightly acidic solution with a pH above the isoelectric point of 7-ACA of the corresponding 7-ACA-carboxylate comprising the steps of adding an acid to the solution in an amount sufficient to precipitate the 7-ACA, and adding an additive to the solution prior to or during addition of the acid, the additive being selected from the group consisting of:

a) organic esters of the formula $$R_1\text{—COO—}R_2 \qquad \text{II}$$

wherein $R_1$ represents hydrogen, unsubstituted or substituted lower alkyl, phenyl, hydroxyphenyl or lower alkylphenyl and $R_2$ represents unsubstituted or substituted lower alkyl, phenyl, hydroxyphenyl or lower alkylphenyl;

b) polymeric glycol compounds of the formula $$H\text{—}(OCHR_1\text{—}CHR_2)_k\text{—}OH \qquad \text{III}$$

wherein in said formula III, $R_1$ is as defined above and $R_2$ denotes hydrogen, unsubstituted or substituted lower alkyl, phenyl, hydroxyphenyl or lower alkylphenyl and k denotes a whole number from 2 to 200;

c) polyacryl derivatives of the general formula $$\text{—[}CHR_1\text{—}CR_2(CO\text{—}XR_3)]_n\text{—} \qquad \text{IV}$$

wherein in said formula IV, X denotes —O— or —NR$_1$— and $R_3$ denotes $R_1$ or —(CR$_2$R$_4$)$_m$—Z, wherein Z denotes $$-\text{N}\begin{array}{c}R_2\\ \\R_4\end{array}-\text{SO}_3\text{H} \quad \text{or} \quad \text{COOH,}$$

m is a whole number from 0 to 6, n is a whole number from 2 to 200,000 and $R_1$, $R_2$, $R_4$ and $R_5$ are the same or different and represent hydrogen, lower alkyl, phenyl, hydroxyphenyl or lower alkylphenyl;

d) amino acids or esters thereof, of the formula $$R_{10}\text{—}CH\text{—}(NR_2R_4)\text{—}COOR_1 \qquad \text{VIII}$$

wherein in said formula VIII, $R_{10}$ denotes hydrogen, unsubstituted or substituted alkyl, unsubstituted or substituted aryl or a group of formula —(CH$_2$)$_m$—X—R$_5$ and $R_1$, $R_2$, $R_4$ and $R_5$ are the same or different and represent hydrogen, unsubstituted or substituted lower alkyl, phenyl, (mono-tri) hydroxyphenyl or lower alkylphenyl, X denotes —O— or —NR$_4$ and m is an integer from 0 to 6.

* * * * *